United States Patent
Souleymanou et al.

(10) Patent No.: US 10,239,852 B2
(45) Date of Patent: Mar. 26, 2019

(54) PROCESS FOR THE PRODUCTION OF 5-HYDROXYMETHYLFURFURAL IN THE PRESENCE OF ORGANIC CATALYSTS FROM THE THIOUREA FAMILY

(71) Applicant: IFP Energies nouvelles, Rueil-Malmaison (FR)

(72) Inventors: Myriam Souleymanou, Lyons (FR); Damien Delcroix, St. Maurice l'Exil (FR)

(73) Assignee: IFP Energies nouvelles, Rueil-Malmaison (FR)

( * ) Notice: Subject to any disclaimer, the term of this patent is extended or adjusted under 35 U.S.C. 154(b) by 0 days.

(21) Appl. No.: 15/747,343

(22) PCT Filed: Jul. 19, 2016

(86) PCT No.: PCT/EP2016/067126
§ 371 (c)(1),
(2) Date: Jan. 24, 2018

(87) PCT Pub. No.: WO2017/016924
PCT Pub. Date: Feb. 2, 2017

(65) Prior Publication Data
US 2018/0370937 A1 Dec. 27, 2018

(30) Foreign Application Priority Data
Jul. 24, 2015 (FR) .................................. 15 57052

(51) Int. Cl.
*C07D 307/50* (2006.01)
*B01J 31/02* (2006.01)

(52) U.S. Cl.
CPC ........ *C07D 307/50* (2013.01); *B01J 31/0245* (2013.01)

(58) Field of Classification Search
CPC ...................... C07D 307/50; B01J 31/0245
See application file for complete search history.

(56) References Cited

FOREIGN PATENT DOCUMENTS

| WO | 2006063220 A2 | 6/2006 |
|---|---|---|
| WO | 2013102911 A1 | 7/2013 |

OTHER PUBLICATIONS

International Search Report PCT/EP2016/067126 dated Sep. 22, 2016.
Kawamoto et al: "Inhibition of acid-catalyzed depolymerization of cellulose with boric acid in non-aqueous acidic media", Carbohydrate Research, Pergamon, GB, vol. 343, No. 2, Nov. 7, 2007 (Nov. 7, 2007), pp. 249-255.
Héctor Quiroz-Florentino et al: "Total synthesis of the natural succinate derivative of 5-(hydroxymethyl) rurfural isolated from the Noni fruit (*Morinda citrifolia*)", Natural Product Research, vol. 23, No. 14, Sep. 20, 2009 (Sep. 20, 2009), GB, pp. 1355-1362.
Florian Ilgen et al: "Conversion of carbohydrates into 5-hydroxymethylfurfural in highly concentrated low melting mixtures", Green Chemistry, vol. 11, No. 12, Jan. 1, 2009 (Jan. 1, 2009), pp. 1948, XP055164377, ISSN: 1463-9262.

*Primary Examiner* — Timothy R Rozof
(74) *Attorney, Agent, or Firm* — Millen, White, Zelano and Branigan, P.C.

(57) ABSTRACT

A process for the transformation of a feed of at least one sugar into 5-hydroxymethylfurfural, contacting the feed with one or more organic catalysts in the presence of at least one solvent, said solvent being water or an organic solvent, alone or as a mixture, at a temperature in the range 30° C. to 200° C., and at a pressure in the range 0.1 MPa to 10 MPa, in which said organic catalysts are selected from compounds from the thiourea family with general formula R1NH—C(=S)—NHR2, in which the groups R1 and R2 are aromatic groups optionally having a heteroatom, linear or branched alkyl groups, which may or may not be cyclic, and alkyl groups with at least one heteroatom, which may be linear or branched, which may or may not be cyclic, said groups R1 and R2 possibly being substituted or unsubstituted and which may be identical or different.

19 Claims, 1 Drawing Sheet

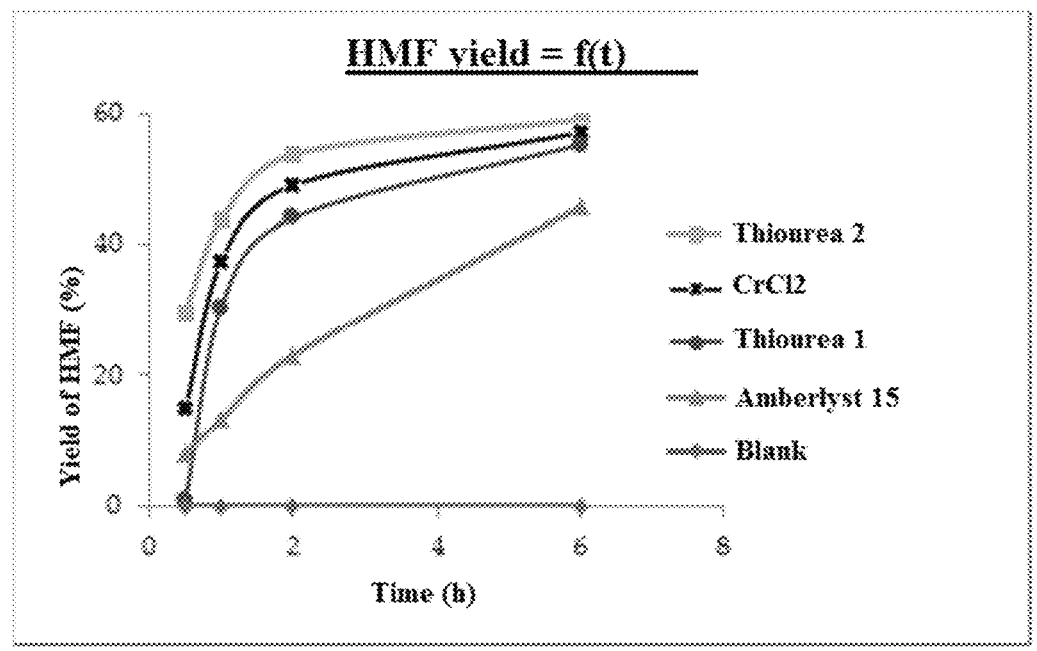

PROCESS FOR THE PRODUCTION OF 5-HYDROXYMETHYLFURFURAL IN THE PRESENCE OF ORGANIC CATALYSTS FROM THE THIOUREA FAMILY

TECHNICAL FIELD OF THE INVENTION

The invention relates to a process for the transformation of sugars, and in particular hexoses, into 5-hydroxymethylfurfural in the presence of novel organic catalysts with low acidity and which are non-corrosive, from the thiourea family.

PRIOR ART 5-hydroxymethylfurfural (5-HMF) is a compound derived from biomass which can be upgraded in a variety of fields as precursors for the active principles in pharmacy, agrochemicals or specialty chemicals. Its importance in recent years resides in its use as a precursor for furandicarboxylic acid (FDCA), which is used, as a substitute for terephthalic acid, as a monomer for the production of polyester fibres or convenience plastics.

The production of 5-HMF by the dehydration of hexoses has been known for many years and has been the focus of a large amount of research. The dehydration of glucose or fructose to 5-HMF with strong Brønsted or Lewis acids has been widely described. The article by Horvath et al. (ACS Catal. 2014, 4, 1470-1477) describes, for example, the transformation of sugars in the presence of sulphuric acid in γ-valerolactone. Heterogeneous sulphonic acids such as Amberlyst resins have also been widely used for the transformation of fructose into 5-HMF, as discussed in detail in the article by Schüth et al. (ACS Catal. 2013, 3, 123-127).

All of these compounds are strong acids, most of which are corrosive as well as toxic; eliminating and recycling them is difficult and may give rise to environmental problems.

The strong acidity of each of these catalysts may be characterized by the numerical value of its pKa in a solvent. As an example, in DMSO, the pKas of sulphuric and sulphonic acids are in the range 0 to 3. As an example, in water, the pKas of sulphuric and sulphonic acids are in the range −14 to −2. These data for the classification of acidity are obtained from the literature and are well known to the person skilled in the art; reference should be made, for example, to the article by F. G. Bordwell et al. (J. Am. Chem. Soc., 1991, 113, 8398-8401).

Thus, there is a need for the development of novel processes using less acidic and less corrosive catalytic systems. Thus, the invention concerns a process for the production of 5-hydroxymethylfurfural from sugars using organic catalysts based on compounds from the family of thioureas, which are less acidic and not corrosive.

SUBJECT MATTER OF THE INVENTION

Thus, in one aspect, the present invention provides a novel process for the transformation of a feed comprising at least one sugar into 5-hydroxymethylfurfural, in which said feed is brought into contact with one or more organic catalysts in the presence of at least one solvent, said solvent being water or an organic solvent, alone or as a mixture, at a temperature in the range 30° C. to 200° C., and at a pressure in the range 0.1 MPa to 10 MPa, in which said organic catalysts are selected from compounds from the thiourea family with general formula R1NH—C(=S)—NHR2, in which the groups R1 and R2 are selected from aromatic groups comprising or not comprising a heteroatom, linear or branched alkyl groups, which may or may not be cyclic, and alkyl groups comprising at least one heteroatom, which may be linear or branched, which may or may not be cyclic, said groups R1 and R2 possibly being substituted or unsubstituted and which may be identical or different.

The term "organic catalyst" means a molecule acting as a catalyst and exclusively containing non-metallic atoms selected, for example, from carbon, hydrogen, oxygen, nitrogen, phosphorus, sulphur, silicon, fluorine, bromine, chlorine and iodine.

One advantage of the present invention is the provision of a process for the transformation of sugars into 5-hydroxymethylfurfural using one or more organic catalysts from the thiourea family, said catalysts having a low acidity, being non-corrosive and being readily recyclable.

DETAILED DESCRIPTION OF THE INVENTION

The Feed

In accordance with the invention, the feed treated in the process in accordance with the invention is a feed comprising at least one sugar, preferably selected from oligosaccharides and monosaccharides, alone or as a mixture.

The term "sugar" means any oligosaccharide or monosaccharide which is soluble under the reaction conditions envisaged for the invention.

The term "monosaccharide" more particularly means carbohydrates with general formula $C_6(H_2O)_6$ or $C_6H_{12}O_6$. Preferred monosaccharides used as a feed in the present invention are selected from glucose, mannose and fructose, used alone or as a mixture.

The term "oligosaccharide" more particularly means a carbohydrate with empirical formula $C_{6n}H_{10n+2}O_{5n+1}$, where n is a whole number greater than 1, the monosaccharide units comprising said oligosaccharide being identical or otherwise, and/or a carbohydrate with empirical formula $(C_{6m}H_{10m+2}O_{5m+1})(C_{5n}H_{8n+2}O_{4n+1})$ where m and n are whole numbers greater than or equal to 1, the monosaccharide units composing said oligosaccharide being identical or otherwise.

The oligosaccharides are preferably selected from oligomers of hexoses or of pentoses and hexoses, preferably from oligomers of hexoses, preferably with a degree of polymerization which allows them to be soluble under the reaction conditions envisaged by the invention. They may be obtained by partial hydrolysis of polysaccharides obtained from renewable resources such as starch, inulin, cellulose or hemicellulose, optionally obtained from lignocellulosic biomass. As an example, steam explosion of the lignocellulosic biomass is a process for the partial hydrolysis of the cellulose and hemicellulose contained in the lignocellulosic biomass, producing a stream of oligosaccharides and monosaccharides.

The preferred oligosaccharides used as a feed in the present invention are preferably selected from saccharose, lactose, maltose, isomaltose, inulobiose, melibiose, gentiobiose, trehalose, cellobiose, cellotriose, cellotetraose and oligosaccharides obtained from the hydrolysis of said polysaccharides obtained from the hydrolysis of starch, inulin, cellulose or hemicellulose, used alone or as a mixture.

Preferably, the feed comprising at least one sugar used in the process in accordance with the invention is selected from cellobiose, fructose and glucose, used alone or as a mixture.

More preferably, said feed comprising at least one sugar used in the process in accordance with the invention is selected from fructose and glucose, used alone or as a mixture.

The Catalysts

In accordance with the invention, in the process of the invention said feed is brought into contact with at least one organic catalyst from the thiourea family in the presence of at least one solvent, said solvent being water or an organic solvent, used alone or as a mixture, at a temperature in the range 30° C. to 200° C., and at a pressure in the range 0.1 MPa to 10 MPa.

In accordance with the invention, the catalyst is selected from compounds from the thiourea family with general formula R1NH—C(=S)—NHR2, in which the groups R1 and R2 are selected from aromatic groups comprising or not comprising a heteroatom, linear or branched alkyl groups, which may or may not be cyclic, and alkyl groups comprising at least one heteroatom, which may be linear or branched, which may or may not be cyclic, said groups R1 and R2 possibly being substituted or unsubstituted and which may be identical or different.

Groups R1 and R2 may be independently selected from families of the groups. As an example, R1 may be selected from aromatic groups and R2 may be selected from cycloalkyl groups.

In the case in which R1 and R2 are selected from the same family of groups, R1 and R2 may be identical or different.

Preferably, said groups R1 and R2 are selected from aromatic groups comprising or not comprising a heteroatom and alkyl groups, which may or may not be cyclic, said groups R1 and R2 optionally being substituted or unsubstituted and which may be identical or different; preferably, said groups R1 and R2 are selected from aromatic groups which do not comprise heteroatoms.

In the case in which said groups R1 and R2 are selected from aromatic groups comprising a heteroatom, said heteroatom is preferably selected from nitrogen, phosphorus and oxygen. In this case, said groups R1 and R2 are preferably selected from the groups pyridine, phosphole and furan.

In the case in which said groups R1 and R2 are selected from aromatic groups not comprising a heteroatom, they are advantageously selected from aromatic groups containing 6 to 14 carbon atoms, which may or may not be fused.

Preferably, the aromatic groups containing 6 to 14 carbon atoms are selected from phenyl, naphthyl, phenanthryl and anthryl groups; more preferably, said group is phenyl.

In the case in which said groups R1 and R2 are selected from alkyl groups, which may be linear or branched, which may or may not be cyclic, they are advantageously selected from alkyl groups containing 1 to 12 carbon atoms, and preferably containing 1 to 6 carbon atoms, and cycloalkyl groups containing 3 to 8 carbon atoms, preferably containing 5 to 8 carbon atoms.

Preferably, the non-cyclic alkyl groups containing 1 to 12 carbon atoms, and preferably 1 to 6 carbon atoms, which may be linear or branched, are selected from the groups methyl, ethyl, propyl, isopropyl, butyl, pentyl and hexyl.

Preferably, the cycloalkyl groups containing 3 to 8 carbon atoms, preferably containing 5 to 8 carbon atoms, are selected from cyclopentyl, cyclohexyl, cycloheptyl and bicyclo[2.2.2]octyl groups.

In the case in which said groups R1 and R2 are selected from alkyl groups comprising at least one heteroatom, which may or may not be cyclic, said heteroatom is preferably selected from nitrogen.

Said groups are thus advantageously selected from alkyl groups and/or cycloalkyl groups which may comprise at least one tertiary amine function. In this case, they are advantageously selected from N,N-dimethylethylamine, N,N-dimethylcyclohexylamine, N-methylpiperidine and aza-bicyclo[2.2.2]octyl.

In the case in which said groups R1 and R2 are substituted, they are preferably substituted with at least one group selected from halogens, —CX$_3$ groups in which X is a halogen, and preferably fluorine, the nitro group —NO$_2$, the group —NHCOCH$_3$, alkoxy groups, preferably selected from methoxy and ethoxy groups, and alkyl groups containing 1 to 12 carbon atoms, which may be linear or branched, preferably selected from methyl, ethyl, propyl, butyl, pentyl and hexyl groups.

Preferably, said groups R1 and R2 are substituted with at least one group selected from halogens, —CX$_3$ groups in which X is a halogen, and preferably fluorine, and alkoxy groups, preferably the methoxy group. Said groups R1 and R2 may advantageously be mono- or disubstituted.

Preferred organic catalysts are advantageously selected from the following organic catalysts: 1-(3,5-bis-trifluoromethyl-phenyl)-3-cyclohexylthiourea, corresponding to the general formula denoted thiourea 1 and with a pKa=10 in DMSO, and 1-(4-methoxyphenyl)-3-phenylthiourea, corresponding to the general formula denoted thiourea 2 and with a pKa=14 in DMSO. The terms "thiourea 1", and "thiourea 2" are exclusive to the text and are intended to simplify writing out these organic catalysts from the thiourea family; the formulae are given below:

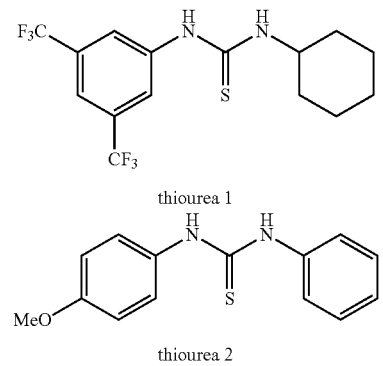

thiourea 1 thiourea 2

In DMSO, the pKas for the organic catalysts from the thiourea family are in the range 8 to 22. Thus, they are much less acidic than the strong acids conventionally used for the dehydration of sugars such as sulphuric acid or sulphonic acids, which have pKas in DMSO in the range 0 to 3. These data for the classification of acidity are obtained from the literature and are well known to the person skilled in the art; reference in this regard may, for example, be made to the article by F. G. Bordwell and al. (J. Am. Chem. Soc., 1991, 113, 8398-8401).

Transformation Process

In accordance with the invention, the process for the transformation of the feed comprising at least one sugar is carried out in a reaction vessel in the presence of at least one solvent, said solvent being water or an organic solvent, alone or as a mixture, at a temperature in the range 30° C. to 200° C. and at a pressure in the range 0.1 MPa to 10 MPa.

The process is thus carried out in a reaction vessel comprising at least one solvent and in which said feed is brought into the presence of at least one organic catalyst from the thiourea family in accordance with the invention.

In accordance with the invention, the process is operated in the presence of at least one solvent, said solvent being water or an organic solvent, alone or as a mixture.

The organic solvents are advantageously selected from alcohols such as methanol, ethanol, propanols, butanols, ethers such as diethylether, dimethoxyethane, tetrahydrofuran, dioxane, esters such as ethyl formate, ethyl acetate, lactones such as γ-valerolactone, γ-butyrolactone, cyclic carbonates such as ethylene carbonate, propylene carbonate, nitriles such as acetonitrile, benzonitrile, amides such as dimethylformamide, diethylformamide, N-methylpyrrolidone, sulphones such as dimethylsulphone, sulpholane, sulphoxides such as DMSO, or ammonium salts such as choline chloride, alone or as a mixture.

In accordance with another embodiment, the process of the invention is operated solely in the presence of an organic solvent.

Preferably, said process in accordance with the invention is operated at a temperature in the range 50° C. to 200° C., and more preferably in the range 50° C. to 175° C., and at a pressure in the range 0.1 MPa to 8 MPa, and preferably in the range 0.1 to 5 MPa.

Generally, the process may be carried out in accordance with various implementations. Thus, the process may advantageously be carried out in batch or in continuous mode. A closed reaction vessel or a semi-open reactor may be used.

The organic catalyst or catalysts from the thiourea family are introduced into the reaction vessel in a quantity corresponding to a weight ratio of feed/organic catalyst(s) in the range 1 to 1000, preferably in the range 1 to 500, preferably in the range 1 to 100, more preferably in the range 1 to 50.

The feed is introduced into the process in a quantity corresponding to a weight ratio of solvent/feed in the range 0.1 to 200, preferably in the range 0.3 to 100 and more preferably in the range 1 to 50.

If a continuous process is selected, the weight hourly flow rate (mass flow rate of feed/mass of organic catalyst(s)) is in the range 0.01 $h^{-1}$ to 5 $h^{-1}$, preferably in the range 0.02 $h^{-1}$ to 2 $h^{-1}$.

At the end of the reaction, the catalyst may readily be recovered by precipitation, distillation, extraction or washing. It may also be recovered by passage over an ion exchange resin such as Amberlyst 15 or Amberlyst 31 and recycled after washing this resin.

The Products Obtained and their Mode of Analysis

The product from the reaction in the transformation process in accordance with the invention is 5-hydroxymethylfurfural.

At the end of the reaction, the reaction medium is analysed by gas phase chromatography (GC) in order to determine the 5-hydroxymethylfurfural content in the presence of an internal calibration and by ion chromatography in order to determine the conversion of the feed in the presence of an external standard.

BRIEF DESCRIPTION OF THE FIGURES

FIG. 1 is a graph representing the change in the yield of the reaction for the production of 5-HMF starting from a sugar feed under different catalytic conditions.

EXAMPLES

In the examples below, the glucose and the fructose used as the feed were commercially available and used without supplemental purification.

The 3,5-trifluoromethylphenyl isothiocyanate, phenyl isothiocyanate, cyclohexylamine and p-anisidine used as precursors for the catalysts in accordance with the invention were commercially available and were used without supplemental purification.

The Amberlyst 15 was commercially available and used without supplemental purification.

The N-methylpyrrolidone, denoted NMP in the examples, used as a solvent, was commercially available and used without supplemental purification.

For Examples 1 and 2 for the preparation of the catalysts from the thiourea family, the molar yield of thiourea was calculated by the ratio between the number of moles of thiourea obtained and the number of moles of isothiocyanate employed.

For Examples 3 to 8 for the transformation of sugars into 5-HMF, the molar yield of 5-HMF was calculated by the ratio between the number of moles of 5-HMF obtained and the number of moles of sugar feed employed.

Example 1: Preparation of the Organic Catalyst Thiourea 1

3,5-trifluoromethylphenyl isothiocyanate (1.485 g, 5.5 mmol) and cyclohexamine (0.595 g, 6 mmol) were dissolved in anhydrous dichloromethane and the reaction medium was stirred overnight at ambient temperature. The solvent was then evaporated off under vacuum and the unrefined product obtained was purified by chromatography on a silica column, the mobile phase being a $CH_2Cl_2$/MeOH gradient. The mass of thiourea 1 obtained was 0.83 g. The molar yield corresponding to thiourea 1 was 41% after purification.

Empirical formula: $C_{15}H_{16}F_6N_2S$; Molecular weight: 370.09 g·$mol^{-1}$ $^1$H NMR (δ (ppm), $(CD_3)_2CO$, 300 MHz) 8.29 (s, 2H), 7.67 (s, 1H), 4.35-4.15 (m, 1H), 1.81-1.54 (m, 4H), 1.45-1.08 (m, 6H)

Example 2: Preparation of Organic Catalyst Thiourea 2

Phenyl isothiocyanate (0.564 g, 4.17 mmol) and p-anisidine (0.510 g, 4.14 mmol) were dissolved in anhydrous dichloromethane and the reaction medium was stirred overnight at ambient temperature. The solvent was then evaporated off under vacuum and the unrefined product obtained was purified by recrystallization from an EtOH/acetone mixture. The mass of thiourea 2 obtained was 0.48 g. The molar yield corresponding to thiourea 2 was 45% after purification Empirical formula: $C_{14}H_{14}N_2OS$; Molecular weight: 258.05 g·$mol^{-1}$ $^1$H NMR (δ (ppm), $(CD_3)_2CO$, 300 MHz) 8.86 (br.s, 1H), 7.54-7.52 (m, 1H), 7.40-7.30 (m, 4H), 7.17-7.13 (m, 1H), 6.94-6.89 (m, 2H), 3.80 (s, 3H).

Example 3: Transformation of Fructose Using the Organic Catalyst Thiourea 1 (in Accordance with the Invention)

The catalyst from Example 1 (0.046 g, 0.12 mmol) was added to a solution of fructose (2.0 g, 11.10 mmol) in NMP (20 g). The feed/catalyst weight ratio was 43.5. The solvent/feed weight ratio was 10. The reaction medium was then stirred at 120° C. for 6 h. The conversion of fructose to 5-HMF was followed by regularly removing an aliquot of solution which was instantly cooled to 0° C., re-dissolved in water and checked by ion chromatography. The 5-HMF yield after 6 h was 55%.

Example 4: Transformation of Fructose Using the Organic Catalyst Thiourea 2 (in Accordance with the Invention)

The catalyst from Example 2 (0.044 g, 0.17 mmol) was added to a solution of fructose (2.0 g, 11.10 mmol) in NMP (20 g). The feed/catalyst weight ratio was 45.5. The solvent/feed weight ratio was 10. The reaction medium was then stirred at 120° C. for 6 h. The conversion of fructose to 5-HMF was followed by regularly removing an aliquot of solution which was instantly cooled to 0° C., re-dissolved in water and checked by ion chromatography. The 5-HMF yield after 6 h was 59%.

Example 5: Transformation of a Mixture of Glucose and Fructose Using the Organic Catalyst Thiourea 1 (in Accordance with the Invention)

The catalyst from Example 1 (0.046 g, 0.12 mmol) was added to a 50% by weight/50% by weight mixture of fructose and glucose (2.0 g, 11.10 mmol) in NMP (20 g). The feed/catalyst weight ratio was 43.5. The solvent/feed weight ratio was 10. The reaction medium was then stirred at 120° C. for 6 h. The conversion of fructose to 5-HMF was followed by regularly removing an aliquot of solution which was instantly cooled to 0° C., re-dissolved in water and checked by ion chromatography. The 5-HMF yield after 6 h was 58%.

Example 6: Transformation of a Mixture of Glucose and Fructose Using the Organic Catalyst Thiourea 2 (in Accordance with the Invention)

The catalyst from Example 2 (0.044 g, 0.17 mmol) was added to a 50% by weight/50% by weight mixture of fructose and glucose (2.0 g, 11.10 mmol) in NMP (20 g). The feed/catalyst weight ratio was 45.5. The solvent/feed weight ratio was 10. The reaction medium was then stirred at 120° C. for 6 h. The conversion of fructose to 5-HMF was followed by regularly removing an aliquot of solution which was instantly cooled to 0° C., re-dissolved in water and checked by ion chromatography. The 5-HMF yield after 6 h was 60%.

Example 7, Comparative: Transformation of Fructose without a Catalyst (not in Accordance)

Fructose (2.0 g, 11.10 mmol) was dissolved in NMP (20 g). The solvent/feed weight ratio was 10. The reaction medium was then stirred at 120° C. for 6 h. The conversion of fructose to 5-HMF was followed by regularly removing an aliquot of solution which was instantly cooled to 0° C., re-dissolved in water and checked by ion chromatography. The 5-HMF yield after 6 h was less than 1%.

Example 8, Comparative: Transformation of Fructose Using a Strong and Corrosive Acid Resin (Amberlyst 15) (not in Accordance)

Amberlyst 15 (0.040 g) was added to a solution of fructose (2.0 g, 11.10 mmol) in NMP (20 g). The feed/catalyst weight ratio was 50. The solvent/feed weight ratio was 10. The reaction medium was then stirred at 120° C. for 6 h. The conversion of fructose to 5-HMF was followed by regularly removing an aliquot of solution which was instantly cooled to 0° C., re-dissolved in water and checked by ion chromatography. The 5-HMF yield after 6 h was 45%.

The results showing the yield of 5-HMF from samples taken after 6 hours of reaction are summarized in Table 1. The results showing the change in the 5-HMF yield over the whole of the reaction period are illustrated in FIG. 1.

TABLE 1

| Example | Feed | Catalyst | Time | Yield (%) |
|---------|------|----------|------|-----------|
| 3 | Fructose | Thiourea 1 | 6 h | 55 |
| 4 | Fructose | Thiourea 2 | 6 h | 59 |
| 5 | Glucose + Fructose | Thiourea 1 | 6 h | 58 |
| 6 | Glucose + Fructose | Thiourea 2 | 6 h | 60 |
| 7 | Fructose | No catalyst | 6 h | <1% |
| 8 | Fructose | Amberlyst | 6 h | 45 |

The reaction kinetics were faster and the 5-HMF yield was higher in the case in which low acidity organic catalysts from the thiourea family in accordance with the invention were used, compared with a strong sulphonic acid such as Amberlyst 15, namely approximately 60% molar yield of 5-HMF in the presence of thioureas, as opposed to 45% for the strong acid resin Amberlyst 15 after 6 hours of reaction.

Thus, it appears that, unexpectedly considering the low acidity, non-corrosive and non-toxic nature of thioureas, it is significantly more advantageous to use the organic catalysts in accordance with the invention compared with a strong acid resin which is conventionally used for the transformation of sugars into 5-HMF.

The invention claimed is:

1. A process for the transformation of a feed comprising at least one sugar into 5-hydroxymethylfurfural, in which said feed is brought into contact with one or more organic catalysts in the presence of at least one solvent, said solvent being water or an organic solvent, alone or as a mixture, at a temperature in the range 30° C. to 200° C., and at a pressure in the range 0.1 MPa to 10 MPa, in which said organic catalysts are selected from compounds from the thiourea family with general formula R1NH—C(=S)—NHR2, in which the groups R1 and R2 are selected from aromatic groups comprising or not comprising a heteroatom, linear or branched alkyl groups, which may or may not be cyclic, and alkyl groups comprising at least one heteroatom, which may be linear or branched, which may or may not be cyclic, said groups R1 and R2 possibly being substituted or unsubstituted and which may be identical or different.

2. The process as claimed in claim 1, in which said sugar is selected from oligosaccharides and monosaccharides, alone or as a mixture.

3. The process as claimed in claim 2, in which the monosaccharides are selected from glucose, mannose and fructose, used alone or as a mixture.

4. The process as claimed in claim 2, in which the oligosaccharides are selected from saccharose, lactose, maltose, isomaltose, inulobiose, melibiose, gentiobiose, trehalose, cellobiose, cellotriose, cellotetraose and oligosaccharides obtained from the hydrolysis of said polysaccharides obtained from the hydrolysis of starch, inulin, cellulose or hemicellulose, used alone or as a mixture.

5. The process as claimed in claim 1, in which said groups R1 and R2 are selected from aromatic groups comprising a heteroatom, said heteroatom being selected from nitrogen, phosphorus and oxygen.

6. The process as claimed in claim 5, in which said groups R1 and R2 selected from the groups pyridine, phosphole and furan.

7. The process as claimed in claim 1, in which said groups R1 and R2 are selected from aromatic groups containing 6 to 14 carbon atoms and not comprising a heteroatom, which may or may not be fused.

8. The process as claimed in claim 7, in which the aromatic groups containing 6 to 14 carbon atoms are selected from phenyl, naphthyl, phenanthryl and anthracyl groups.

9. The process as claimed in claim 1, in which said groups R1 and R2 are selected from non-cyclic alkyl groups containing 1 to 12 carbon atoms, which may be linear or branched, selected from the groups methyl, ethyl, propyl, isopropyl, butyl, pentyl and hexyl.

10. The process as claimed in claim 1, in which said groups R1 and R2 are selected from cycloalkyl groups containing 3 to 8 carbon atoms selected from cyclopentyl, cyclohexyl, cycloheptyl and bicyclo[2.2.2]octyl groups.

11. The process as claimed in claim 1, in which said groups R1 and R2 are selected from alkyl groups and/or cycloalkyl groups comprising at least one tertiary amine function.

12. The process as claimed in claim 11, in which said groups R1 and R2 are selected from N,N-dimethylethylamine, N,N-dimethylcyclohexylamine, N-methylpiperidine and aza-bicyclo[2.2.2]octyl.

13. The process as claimed in claim 1, in which said organic catalyst is 1-(3,5-bis-trifluoromethylphenyl)-3-cyclohexyl thiourea.

14. The process as claimed in claim 1, in which said organic catalyst is 1-(4-methoxyphenyl)-3-phenyl thiourea.

15. The process as claimed in claim 1, in which said solvent is an organic solvent selected from alcohols, ethers, esters, lactones, cyclic carbonates, nitriles, amides, sulphones, sulphoxides and ammonium salts, alone or as a mixture.

16. The process as claimed in claim 15, in which the alcohols are selected from methanol, ethanol, propanols and butanols, and in which the ethers are selected from diethylether, dimethoxyethane, tetrahydrofuran and dioxane, and in which the esters are selected from ethyl formate and ethyl acetate, and in which the lactones are selected from γ-valerolactone and γ-butyrolactone, and in which the cyclic carbonates are selected from ethylene carbonate and propylene carbonate, and in which the nitriles are selected from acetonitrile and benzonitrile, and in which the amides are selected from dimethylformamide, diethylformamide and N-methylpyrrolidone, and in which the sulphones are selected from dimethylsulphone and sulpholane, and in which the sulphoxide is DMSO, and in which the ammonium salt is choline chloride, alone or as a mixture.

17. The process as claimed in claim 1, in which the temperature is in the range 50° C. to 200° C., and in which the pressure is in the range 0.1 MPa to 8 MPa.

18. The process as claimed in claim 1, in which the feed is introduced in a solvent/feed weight ratio in the range 0.1 to 200.

19. The process as claimed in claim 1, in which the organic catalysts from the thiourea family are introduced in a feed/organic catalyst(s) weight ratio in the range 1 to 1000.

* * * * *